United States Patent
Gilby

(12) 
(10) Patent No.: US 6,342,948 B1
(45) Date of Patent: Jan. 29, 2002

(54) DUAL PATHLENGTH SYSTEM FOR LIGHT ABSORBANCE DETECTION

(75) Inventor: Anthony C. Gilby, Foxborough, MA (US)

(73) Assignee: Waters Investments Limited

( * ) Notice: Subject to any disclaimer, the term of this patent is extended or adjusted under 35 U.S.C. 154(b) by 0 days.

(21) Appl. No.: 09/196,579

(22) Filed: Nov. 20, 1998

(51) Int. Cl.$^7$ ............................................. G01N 21/00
(52) U.S. Cl. ........................ 356/436; 356/246; 356/440
(58) Field of Search ............................... 356/432–440, 356/244, 246; 250/343, 345, 346, 338.5, 252.1

(56) References Cited

U.S. PATENT DOCUMENTS

| | | |
|---|---|---|
| 2,761,067 A | 8/1956 | Troy |
| 3,652,850 A | 3/1972 | Briggs |
| 3,743,426 A | 7/1973 | Steinberg |
| 4,120,592 A | 10/1978 | Fleming et al. |
| 4,157,470 A | 6/1979 | Kotaka et al. |
| 4,288,693 A | 9/1981 | Fabinski et al. |
| 4,496,840 A | 1/1985 | Fabinski et al. |
| 5,146,294 A | 9/1992 | Grisar et al. |
| 5,153,679 A * | 10/1992 | Gilby ........................ 356/440 |
| 5,184,192 A * | 2/1993 | Gilby et al. ................. 356/246 |
| 5,214,593 A | 5/1993 | Magnussen et al. |
| 5,486,699 A | 1/1996 | Fabiniski et al. |
| 5,517,314 A | 5/1996 | Wallin |
| 5,602,647 A * | 2/1997 | Xu et al. .................... 356/435 |
| 5,689,114 A | 11/1997 | Miyazaki et al. |
| 5,815,258 A | 9/1998 | Nakanishi |

OTHER PUBLICATIONS

R.D. Harris, et al. Integrated Optical Surface Plasmon Resonance Biosensor for Pesticide Analysis.

* cited by examiner

*Primary Examiner*—Hoa Q. Pham
(74) *Attorney, Agent, or Firm*—Anthony J. Janiuk

(57) ABSTRACT

A flow cell for absorbance detection with at least two different optical path lengths. It increases the range of analyte concentrations which can be measured compared with a conventional single path flow cell. Light from the two paths is combined onto the same photodetector. Calibration with known samples allows analyte concentrations to be measured. The dual or multi-path length flow cell may be used in equipment designed for single path flow cells.

27 Claims, 13 Drawing Sheets

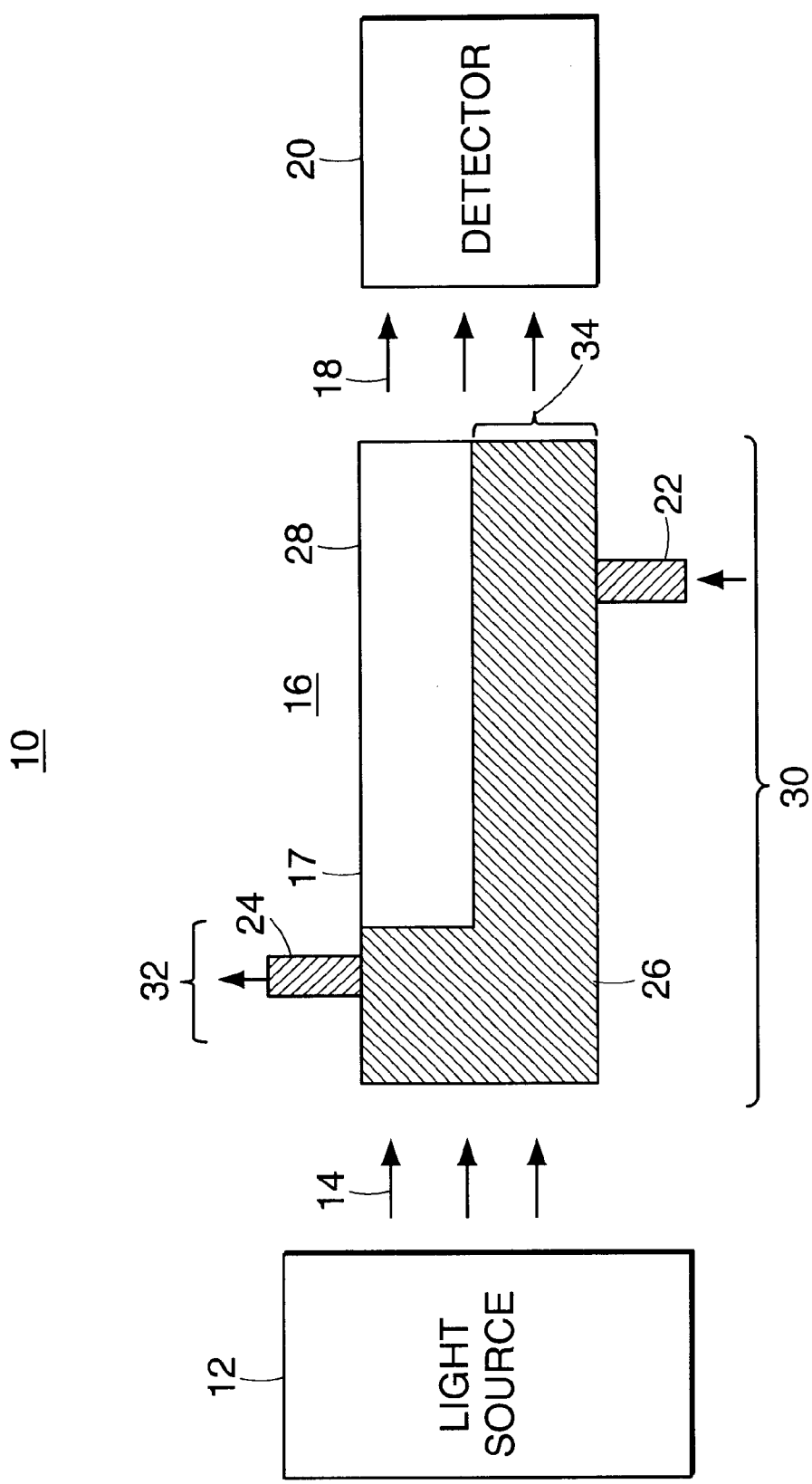

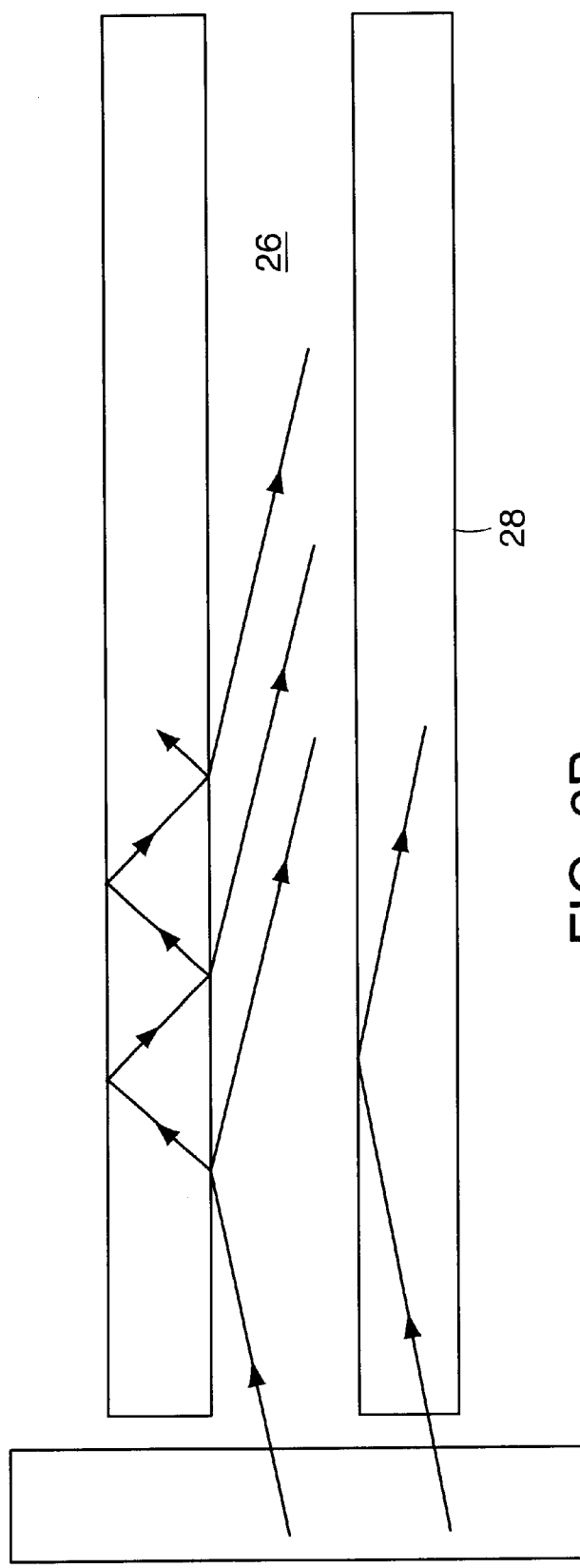

FIG. 10. DUAL PATH CELL ANALYTICAL PRECISION: b=50 mm, b.j.=0.5. X=0.8. MOLAR ABSORPTIVITY 10,000 cm-1(mol/L)-1. FROM BOTTOM, 1: Am=0, k=0.1%. 2: Am=0.2, k=0.1%. 3. Am=0.5, k=0.1%. 4: Am=1, k=0.1%.

DUAL PATHLENGTH SYSTEM FOR LIGHT ABSORBANCE DETECTION

FIELD OF THE INVENTION

The present invention relates to liquid chromatography instrumentation, and more particularly to a method and apparatus for absorbance detectors allowing multiple pathlength flow cells.

BACKGROUND OF THE INVENTION

Absorbance detectors are useful in high performance liquid chromatography (HPLC). Broad spectrum or bandwidth limited light is directed through a sample, and then measured at the chosen analytical wavelengths by a detector, such as a photodetector. In a traditional instrument, light traverses a fixed distance (path length) through the sample. The instrument's photodetector signal is measured when the analyte sample concentration is zero ($I_0$) and when the analyte is present (I). Absorbance (A), a dimensionless number expressed in absorbance units, a.u., is calculated from $\log(I_0/I)$ and displayed as the instrument output. Absorbance is proportional to the product of pathlength (b) and concentration (c)-Beer's Law. The constant of proportionality can be found from a calibration experiment using known analyte concentrations, thus enabling unknown concentrations to be measured.

If pathlength is expressed in cm and concentration in moles/L, the proportionality constant is called the molar absorbtivity ($\epsilon$) with units $cm^{-1}$ $(moles/L)^{-1}$.

Since $\epsilon$ varies with wavelength for any analyte, the instrument includes a monochromator, filters, a diode array spectrograph or, in the case of the infrared a Fourier transform interferometer, so that absorbance is measured at specific wavelengths.

The range of concentrations of an analyte which can be measured in such an instrument is limited. At the low end, the minimum detectable change in absorbance is set by the base line noise on the absorbance output, a value which varies from wavelength to wavelength and from instrument to instrument. A well-designed UV absorbance detector for HPLC can detect an absorbance change in the region of 10 to 20μa.u. An upper limit of concentration measurement is reached when the relationship between absorbance and concentration becomes significantly nonlinear. This typically occurs when absorbance exceeds 1 to 2 a.u. The upper absorbance limit is usually the result of stray light or inadequate spectral resolution. The upper absorbance limit varies with wavelength and from instrument to instrument, and is reduced if the solvent or HPLC mobile phase absorbs.

The analyte concentration range as used herein is defined as the ratio of the maximum to minimum concentration. Because of the above, it is limited to about five orders of magnitude. If the goal is to quantitate to 1%, the analyte concentration range (assuming comparable molar absorptivities among components) cannot exceed three decades. This can result in the need for more than one HPLC run with different sample injections in order to quantitate major components and trace impurities in a sample mixture.

Beer's Law shows that lower concentrations can be detected if the cell pathlength is increased, and higher concentrations will fall within the linear absorbance range if the pathlength is decreased. But changing the pathlength will in itself neither increase nor decrease the concentration range.

Further, cell detector design is close to limits imposed by the physics of available components (light sources, photo detectors etc.), the constraints on cell volume required to maintain chromatographic resolution, and market-driven requirements of spectral range and resolution. It is already a challenge to build detectors and chromatographic systems which do not have some spurious source of noise in excess of the value set by physics. Even if the theoretical noise could be reduced by improved design, such significantly lower noise may not be realized in practice.

Long pathlength light-guiding flowcells offer a way to increase concentration sensitivity for a given baseline noise. Unfortunately, the high concentration limit, set by the detector's linear absorbance range, is reduced by the same amount, so that the concentration range remains the same. As previously noted, if the mobile phase absorbs, the concentration range will actually be less with a longer cell.

Wide concentration range is a very important attribute of a detector. It enables major components and trace impurities (as in a drug formulation) to be quantitated in a single injection. In this application of an analytical scale separation, a wide concentration range, using larger injections of sample, is more useful than the ultimate in low detection limits.

Providing dual pathlengths to measure a wider range of concentrations has been attempted with varying degrees of success. U.S. Pat. No. 5,214,593 (Magnussen) discloses a method of using multi-pathlength flow cells using at least two light beams and at least two photo detectors. Light which passes through a standard length sample cell impinges on a sample photodiode and light which passes through a (shorter) reference cell impinges on a reference photodiode. At low sample concentrations the detector behaves like a conventional dual beam instrument with very little sample-induced change in the reference photodiode signal. At high concentrations, the sample photodiode signal falls to zero and the instrument's reference beam behaves like a single beam detector. The signal processing electronics select the photodiode output appropriate to the concentration range. Each pathlength has its own light beam and detector. The two detectors produce signals which are processed separately and then combined. This requires expensive redundancy in equipment, and would be particularly expensive to implement using photodiode array detectors.

In fact, as shown in FIGS. 1, 2 and 3 of Magnussen the use of three detectors is preferred, with the third detector serving as a reference. This can greatly increase the cost of the apparatus.

Further, Magnussen requires the apparatus to be especially designed to perform multi-pathlength flow cell analysis. The instrument must be built with multiple light beams, multiple light detectors, and multiple channels for detector signal processing. The implementation taught by Magnussen can not be used in existing single-pathlength systems.

U.S. Pat. No. 4,120,592 (Flemming) discloses a multiplex optical analyzer apparatus. The apparatus uses multiple path lengths with a single light source and detector. The light beam only passes through one cell pathlength at a time, by the action of a light spectrum filter wheel and spectrum sensitive beam splitters, as shown in FIG. 1 of Flemming. Thus Flemming only measures one pathlength at a time, requiring extra time for analyzing samples. Also, similar to Magnussen, Flemming requires a specially designed system to perform multi-pathlength flow cell analysis.

SUMMARY OF THE INVENTION

The present invention provides a dual or multi-path length flow cell wherein light from the different sample pathlengths is combined and impinges on the same photodetector. This implementation can be used with photodiode array detectors which conventionally have only a single cell and a single photodiode array.

According to a dual pathlength embodiment of the present invention, a flow cell is provided in which a portion of the light traverses a long pathlength and the balance of the light traverses a much shorter pathlength. Light entering the flow cell is split between the two paths and then recombined to be passed to the photodetector. The dual path flow cell can in principle replace the single path cell in a spectrometer or detector. At low analyte concentrations, changes in light transmission in the long path portion of the cell are sensitive to small changes in concentration. The slope of the calibration curve, A versus c, is high in this region. At high concentrations the long path becomes opaque and the detector response depends on light in the short path. The slope A versus c is proportional to pathlength and is much less when the short path length dominates. At intermediate concentrations, the slope transitions between these two regions.

Because the overall curve of A versus c is nonlinear, a much wider range of concentrations falls within the limited absorbance range of the detector. Once the instrument response versus concentration of a particular analyte is characterized, the instrument can be used for quantitative analysis. The length ratio of the two paths can be quite large, on the order of 100:1. Other than the form of the algorithm to compute sample concentration discussed in detail hereinafter, there is no change in the operation of the detector or spectrometer using the dual path length flow cell according to the invention. The concepts according to the invention are related herein to absorbance detectors for high performance liquid chromatography (HPLC), but are equally applicable to bench-top spectrophotometers.

Features of the invention include provision of a multipath flow cell that increases the range of analyte concentration that can be measured in an absorbance detector by combining light which has traversed at least two different sample pathlengths. The quantity and cost of related equipment is minimized according to the invention in that a single detector is used to receive light that passes through each of the varied length multiple paths.

The present invention provides the ability to use multipath flow cells in a traditional single path system thereby providing expanded capablities of present equipment.

BRIEF DESCRIPTION OF THE DRAWING

The foregoing and other features and advantages of the present invention will be more fully understood from the following detailed description of illustrative embodiments, taken in conjunction with the accompanying drawings in which:

FIG. 1 is a conceptual overview of a dual-pathlength measurement system according to the present invention;

FIGS. 2A and 2B are flow cells for use in an illustrative embodiment of the present invention;

DETAILED DESCRIPTION

Figure 2A:
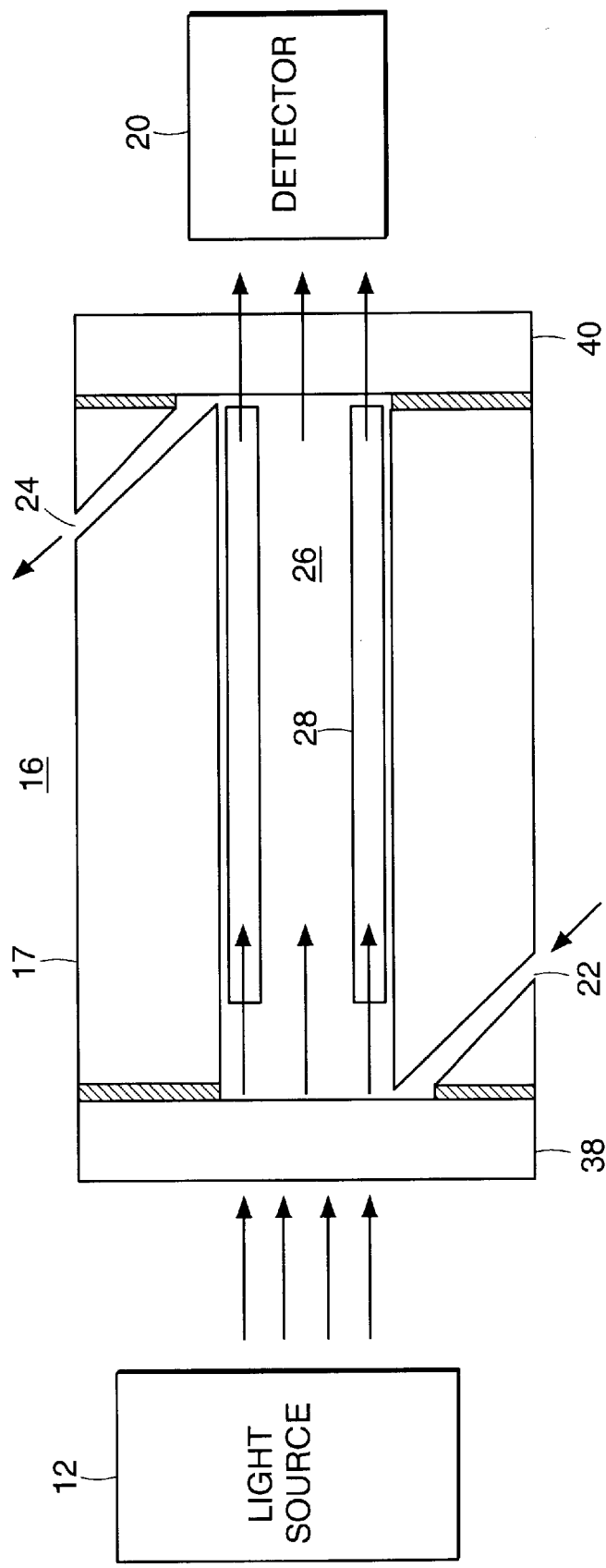

A conceptual overview of a dual-pathlength measurement system 10 according to the present invention is shown in FIG. 1. A light source 12 provides light beams 14 which pass into and through a flow cell 16. The light source 12 is any light source providing light of the proper spectrum and bandwidth, including a Deuterium Lamp. The light source 12 may also include focusing lenses and reflectors (not shown).

As the light beams 14 enter the flow cell 16, they pass through the sample in the chamber 26. The sample flows into the flow cell through the inlet 22 and outlet 24. After passing though the flow cell 16, the light beams 18 are detected and measured by a detector 20; which includes various types of light detectors such as a silicon photodiode or photodiode array. In the case of a photodiode array detector, the combined light 18 is wavelength dispersed before it reaches the photodiode array. An illustrative detector is the 996 Photodiode Array Detector produced by Waters Corp. of Milford, Massachusetts. All the light beams 18 which have passed through the flow cell 16 are detected by the same detector 20, which produces an output signal indicative of the light as affected by the sample in the chamber 26.

The flow cell 16 is partitioned by a portion 28, which admits none of the sample therein, but does allow the passage of light. This creates two path lengths for the light to traverse, a short path length as shown by 32, and a long path length as shown by 30. The portion 28 may be a solid transparent material, or contain gas or even a vacuum.

The width 34 of the long path 30 is selected to determine what percentage of the light passes through sample in the chamber 26 on the long path 30 versus the short path 32. Selection of this ratio will be discussed below.

An illustrative embodiment of a flow cell 16 according to the present invention is shown in FIG. 2A. This flow cell 16 can be inserted into a high performance liquid chromatography (HPLC) system which normally takes a conventional flow cell with a single pathlength, thereby allowing existing HPLC equipment to perform multi-pathlength analysis. In fact this flow cell 16 can be a regular single path flow cell that is modified according to the invention.

Figure 3B:
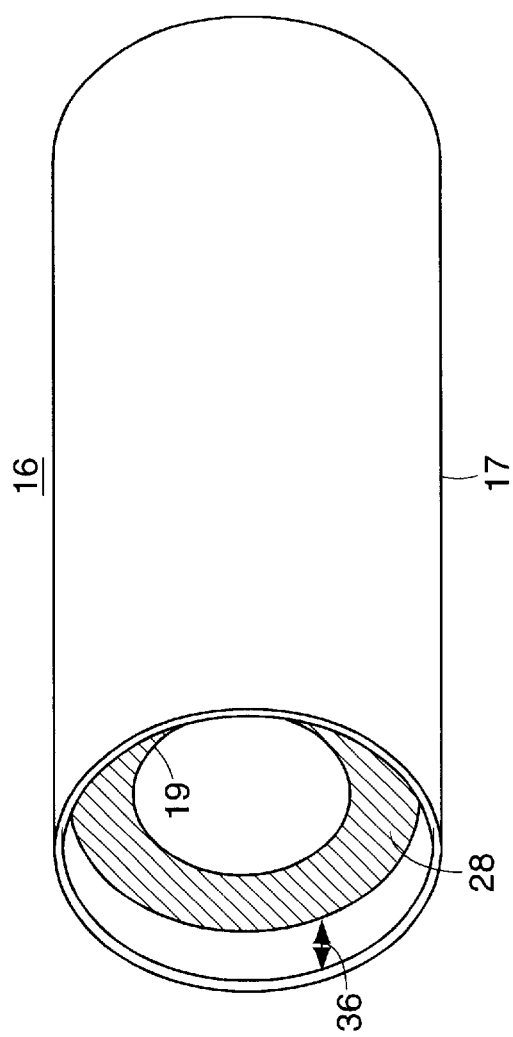
FIGS. 3A and 3B show details of the flow cell of FIG. 2.
Figure 3A:
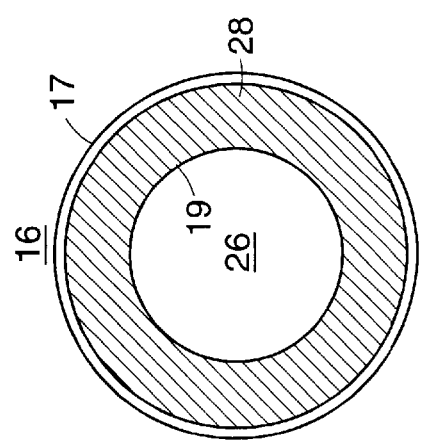

The flow cell 16 is cylindrically shaped with an outer wall 17 and two transparent end sections 38 and 40. The outer wall has a thickness that defines the sample chamber 26. The inside surface of the outer wall 17 of the flow cell is coated with Teflon AF or is lined with Teflon AF tubing to create a light guiding pathway. The sample chamber 26 has a tube 28 disposed therein which allows the passage of light without passing through the sample in the sample chamber interior to the tube. The tube 28, inserted within the outer wall 17, is illustrated in greater detail in FIGS. 3A and B. Preferably, the tube 28 is a piece of fused silica capillary tubing, although any light transparent solid material may be used.

The inside surface 19 of the tube 28 is coated with Teflon AF, known for its light guiding properties, so that light which enters the sample chamber (bore) 26 is effectively confined to the bore. Thus two light paths are formed, one through the bore 26 and a second through the wall of the tube 28. Light is segregated during passage through the flow cell, FIG. 2 in the first and second flow paths.

Alternatively, the tube 28 may be uncoated. The light would then follow a more complicated path or plurality of paths through the sample. Light which entered the end of the tube 28 would traverse the short path and be guided within the tube 28 to the end, due to the greater index of refraction of the tube 28 versus the sample in chamber 26. A portion of the light, probably small, would be absorbed by the sample by attenuated total reflection at the internal point of reflection where tube 28 contacts the sample. The effect of this is a small addition to the effective path length of the short path. On the other hand, some of the rays which initially entered the long path may strike the internal bore of tube 28. A portion of these rays will refract into the silica wall of tube 28, spending more or less time in the silica before re-emerging into the liquid of the long path. These rays therefore travel paths through the liquid which are intermediate the long and short paths. The response of such a cell to changes in sample concentration may be established using a series of calibration samples.

By way of example, in a multiple pathlength embodiment with greater than two path lengths, a structure such as illustrated in FIG. 2B (substantially similar to that illustrated in FIG. 2A), is constructed without interior coatings to guide the light and form the two distinct flow paths of different lengths as described in detail hereinbefore. In this example, a top light ray enters and traverses long pathlengths, while a bottom ray traverses a short path. In such an embodiment, the multiple light paths merge in their passage through the cell, forming a geometrical progression of branching rays, traversing the cell in paths of varying lengths.

A low index coating such as Teflon AF on the interior of the tube 28 would substantially prevent light rays entering the tube 28 from entering the long pathlength. Light in the short pathlength which entered the wall of the tube 28 would be guided in the tube wall regardless of whether there was any coating on the interior surface of the outer wall 17 of the flow cell body. Thus multiple pathlengths could be effected as well by a light guiding material disposed on the inside of the tube, without providing a light guiding material on the inside surface of the outer wall of the flow cell.

Another option if tube 28 is uncoated is to use taper beam or reversed taper beam techniques (such as described in U.S. Pat. No. 5,153,679 which is incorporated herein by reference), to confine light in the long path to the fluid filled bore. Optics to create a taper beam are incorporated in the Waters 2487 dual wavelength tunable UV-visible absorbance detector, and optics to create a reversed taper beam are incorporated in Waters 996 photodiode array detector. The flowcell of HPLC detectors such as these can be modified to a dual pathlength cell of the present invention using a simple uncoated light transmitting tube inserted into the cell bore. Cells of the present invention with longer pathlengths and smaller volume than conventional analytical scale HPLC cells are better constructed using a flowcell chamber whose inner wall is lined with Teflon AF (such as described in U.S. Pat. No. 5,184,192 owned by the assignee of the present invention and incorporated herein by reference). higher light throughput to be maintained.

For ease of manufacturing, the tube 28 (illustrated in views in FIGS. 3A and 3B), should not extend all the way to the cell end window 40 (best illustrated in FIG. 2A). This avoids blocking of the outflow port 24. Therefore the tube 28 can be a solid tube, while the inflow and outflow ports 22 and 24 function properly. The flowcell body and inlet and outlet ports can be constructed from materials such as 316 stainless steel or PEEK (polyetheretherketone). The end windows 38 and 40, which can be flat or curved, in the illustrative embodiment are made from fused silica. The dimensions of the tube 28 in the illustrative embodiment include an inner diameter (ID) of approximately 1mm, and an outer diameter (OD) of approximately 2 mm. The illustrative tube 28 is dimensioned to provide a long path 30 approximately 10–20 mm long and a short path 32 approximately 0.2 mm long. For practical purposes, a range of ratios of long path to short path of 50:1 to 100:1 could be implemented, or perhaps even a more extreme range of 2:1 to 1000:1. Cells with widely differing dimensions can be made to suit the application, for example to span the range from preparative to microbore chromatography.

Figure 4:
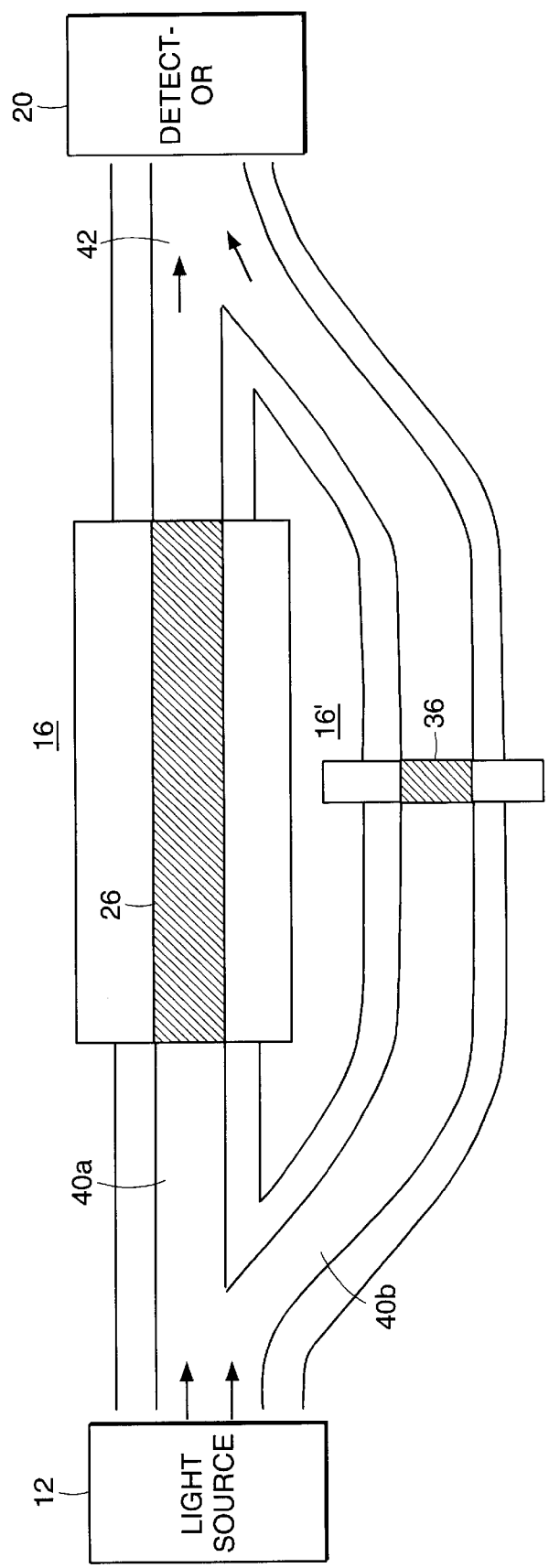
FIG. 4 is an alternative embodiment according to the present invention.

An alternative embodiment according to the present invention is shown in FIG. 4. Here, light is directed along dual paths 40a and 40b by a Fiber Optic (FO) cable into two separate flow cells 16 and 16', after which the light is recombined into a single path 42 to the detector 20. The two flow cells 16 and 16' include plumbing to provide the sample concentration to both flow cells (not shown). Other techniques may be used to divide, guide and recombine the light along paths 40, including mirrors, semisilvered mirrors, prisms, beam splitters, or the like.

The absorbance characteristics of a dual path cell according to the present invention will now be discussed with reference to FIG. 5. The case of a single path cell is reviewed first to lead into the dual path explanation.

For a single path cell, the absorbance is defined by $$A=\log(I_0/I)=\log(e^{abc})=a.b.c.\log(e) \quad (Eq.1)$$

and $$A=\epsilon.b.c \text{ so that } \log(e).a=0.434a=\epsilon \quad (Eq.2)$$

where a is the absorption coefficient; b is the pathlength; c is the concentration of analyte in mols/liter (M/L); and $\epsilon$ is the molar absorptivity, $cm^{-1}(M/L)^{-1}$.

If the mobile phase is transparent, the photodetector signal in the absence of analyte is $I_0$. If the mobile phase absorbs, the signal is Im. In a single path cell, of length b, the absorbance and transmittance of the mobile phase are:

$$A_m=\log(I_0/I_m) \text{ and } I_m/I_0=10^{-Am}. \quad (Eq.3)$$

Standard practice is to zero the detector absorbance output with pure mobile phase in the cell. The transmittance of the analyte concentration c is then $I/I_m$. Both I and $I_m$ are reduced by mobile phase absorption so that:

$$I=I_0.10^{-Am}.e^{-abc} \text{ and } I_m=I_0.10^{-Am}. \quad (Eq.4)$$

These are combined to yield sample transmittance and absorbance:

$$I/I_m=(I_0.10^{-Am}.e^{-abc})/(I_0.10^{-Am}) \quad (Eq.5)$$

$$A=\log(I^m/I)=\log[(I_0.10^{-Am})/(I_0.10^{-Am}.e^{-abc})]=\log[e^{abc}]=a.b.c.\log(e)=\epsilon.b.c \text{ as if } A_m \text{ were zero} \quad (Eq.6)$$

Mobile phase absorption does not affect the slope of the calibration curve, A versus c. However, a non-zero value for $A_m$ cuts down the signals, which causes the absorbance noise to rise, and this reduces the low-concentration sensitivity.

Now a stray light term is added. Stray light is added to the photodetector signal whether or not there is absorbing mobile phase or sample in the cell. In other words the stray light is assumed to be at a wavelength which is not absorbed. The stray light contribution taken as a fraction of the light available for measurement at a particular analytical wavelength is $k.I_0$. The value of k will vary with analytical wavelength. Analyte transmittance and absorbance are:

$$I/Im = (I_0.10^{-Am}.e^{-\alpha bc} + k.I_0)/(I_0.10^{-Am} + k.I_0) \quad (Eq.7)$$

$$A = \log(I_m/I) = \log[(1+k.10^{Am})/(e^{-\alpha bc} + k.10^{Am}))] \quad (Eq.8)$$

At concentrations below the stray light roll-off (k=0 in Equation 8):

$$A = \log[1/e^{-\alpha bc}] = \log(e).\alpha.b.c = \epsilon.b.c \quad (Eq.9)$$

And again, the slope of the curve is unaffected by mobile phase absorption.

At high concentrations, and with $k.10^{Am}$ much less than 1, Equation 8 gives:

$$A_{roll-off} = \log(1/k.10^{Am}) = \log(1/k) - A_m \quad (Eq.10)$$

Equation 10 shows that the effect an absorbing mobile phase has on the high-c roll-off can be viewed in either of two ways. The roll-off absorbance is reduced by $A_m$, or the stray light is amplified by the factor $10^{Am}$.

In summary, mobile phase absorption in a single path cell reduces low-end sensitivity by increasing noise, and at the high end, amplifies the effect of stray light to reduce linear range. Both effects reduce the concentration range of an absorbance detector.

Figure 6:
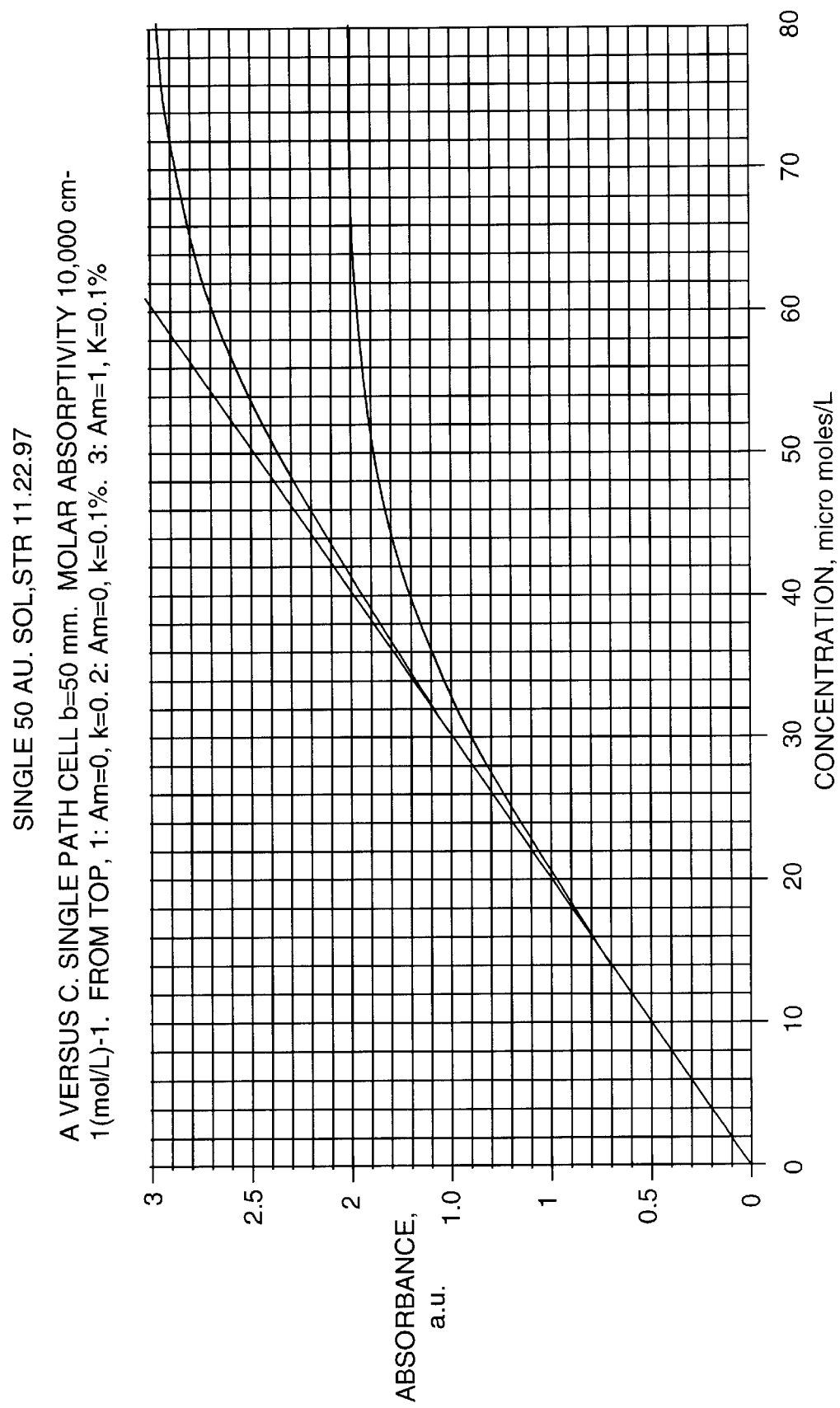
FIG. 6 is a graph illustrating A versus c for a single path flow cell.

The calibration curve as shown in FIG. 6, A versus c, has slope b.ε before the stray light rolloff and a zero intercept. (The detector absorbance output is normally zeroed when c=0).

For dual pathlength cells, development of the A versus c expression follows the same steps as the single path cell as described above.

With transparent solvent (mobile phase) in the cell, the photodetector signal is $I_0$. Fraction X of the light emerges from long path b and (1−X) from the short path j.b.

The photodetector signal with analyte concentration c is the sum of contributions from the two paths:

$$I = X.I_0.e^{-\alpha bc} + (1-X).I_0.e^{-\alpha jbc} \quad (Eq.11)$$

$$A = \log(I_0/I) = \log.[1/(X.e^{-\alpha bc} + (1-X).e^{-\alpha jbc})] \quad (Eq.12)$$

Now add the effect of mobile phase absorption. The signal with pure mobile phase in the cell is:

$$I_m = X.I_0.10^{-Am} + (1-X).I_0.10^{-jAm} \quad (Eq.13)$$

The transmittance of the analyte in mobile phase, relative to the mobile phase alone is:

$$I/I_m = (X.I_0.10^{-Am}.e^{-\alpha bc} + (1-X).I_0.10^{-jAm}.e^{-\alpha jbc})/(X.I_0.10^{-Am} + (1-X).I_0.10^{-jAm}) \quad (Eq.14)$$

Addition of a stray light term completes the equation:

$$I/I_m = (X.I_0.10^{-Am}.e^{-\alpha bc} + (1-X).I_0.10^{-jAm}.e^{-\alpha bc+kJ}_0)/(X.I0.10^{-Am} + (1-X).I_0.10^{-jAm} + k.I_0) \quad (Eq.15)$$

$$= /(X.10^{-Am}.e^{-\alpha bc} + (1-X).10^{-jAm}.e^{\alpha jbc} + k)/(X.10^{-Am} + (1-X).10^{-jAm} + k)$$

Figure 5:
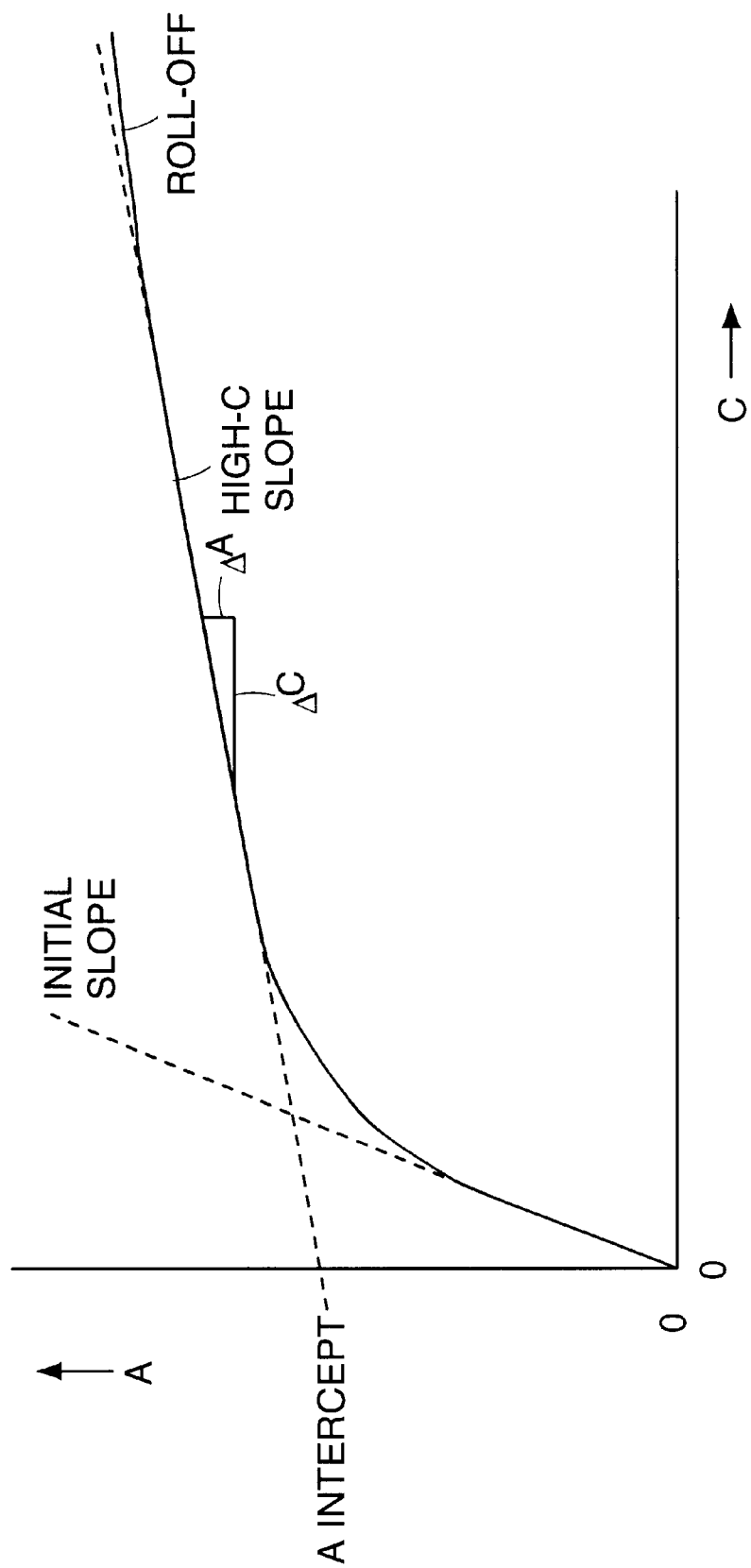
FIG. 5 is a graph illustrating a generalized calibration curve of A versus c.

The equation for the dual path cell calibration curve can now be described for absorbance A in terms of analyte concentration c (FIG. 5).

$$A = \log(I_m/I) = \log[(X.10^{-Am+}(1-X).10^{-jAm} + k)/(X.10^{-Am}.e^{-\alpha bc} + (1-X).10^{-jAm}e^{-\alpha jbc+k)}] \quad (Eq.16)$$

Differentiation of Equation 16 gives the slope of the calibration curve:

$$dA/dc = \alpha.\log(e).b.(X.10^{-Am}.e^{-\alpha bc} + j.(1-X).10^{-jAm}.e^{\alpha jbc})/(X.10^{-Am}.e^{-\alpha bc} + (1-X).10^{-jAm}.e^{-\alpha jbc} + k) \quad (Eq.17)$$

Figure 8A:
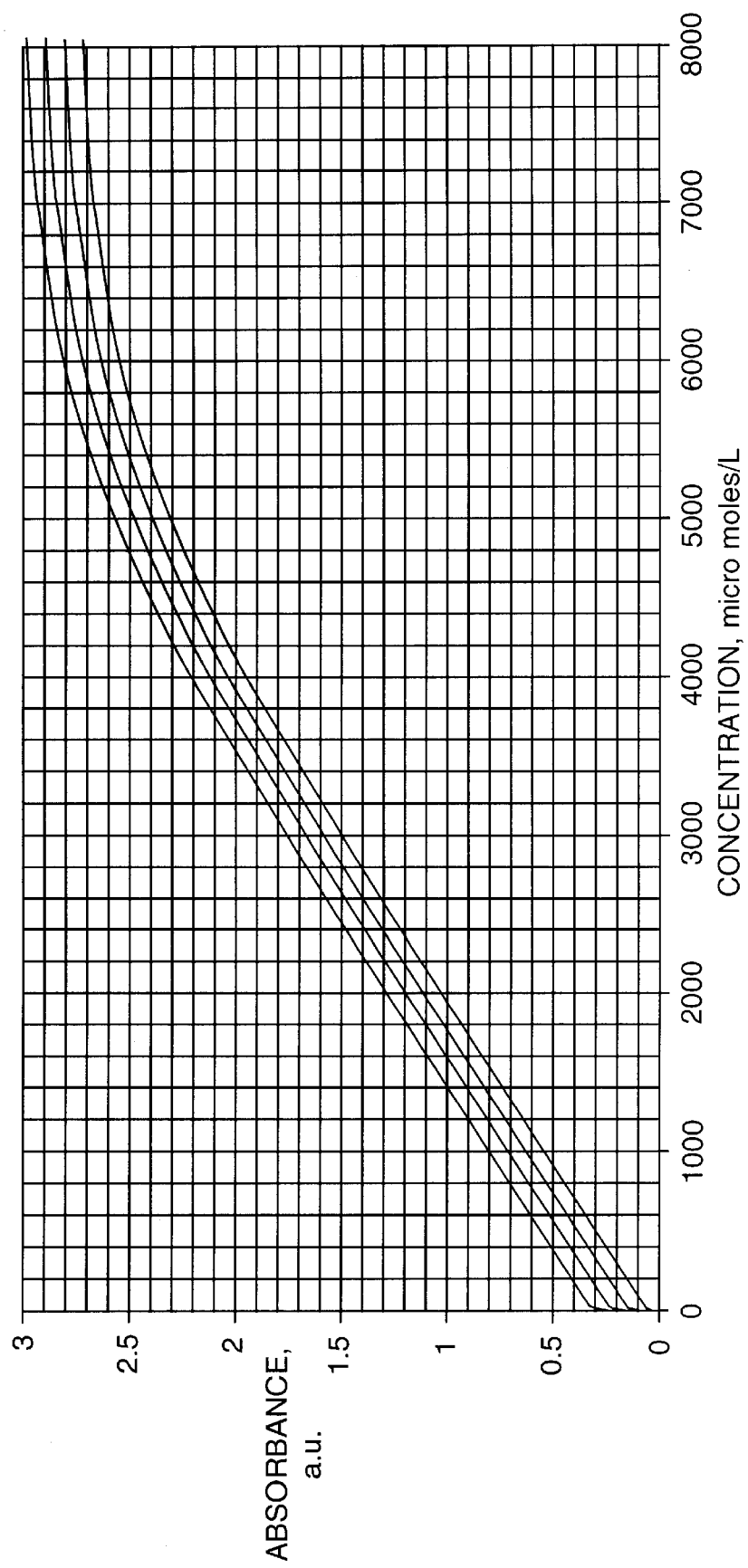
FIGS. 8A, 8B and 8C are graphs illustrating A versus c with stray light for a dual path flow cell according to the present invention.
Figure 8B:
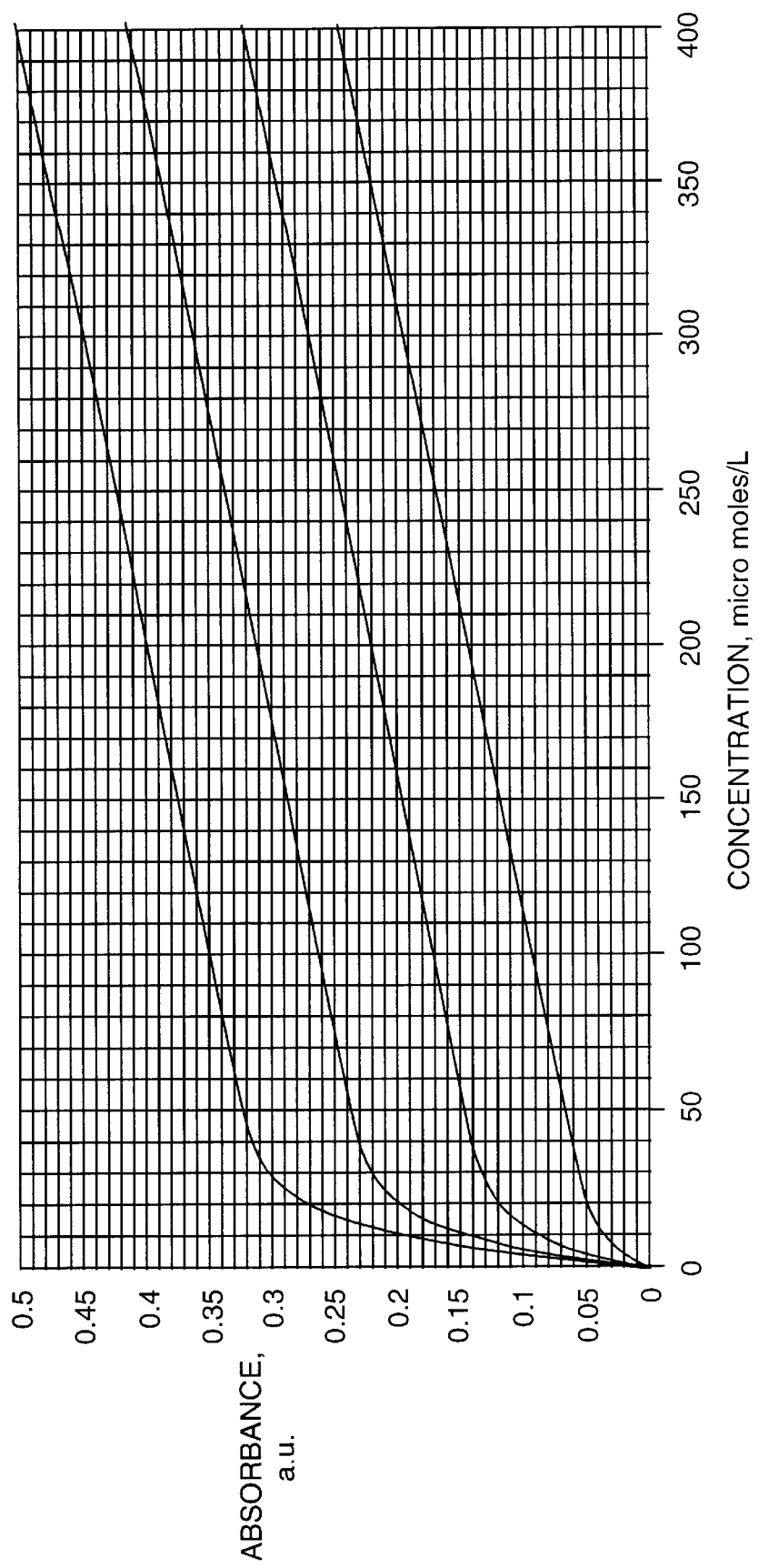
Figure 8C:
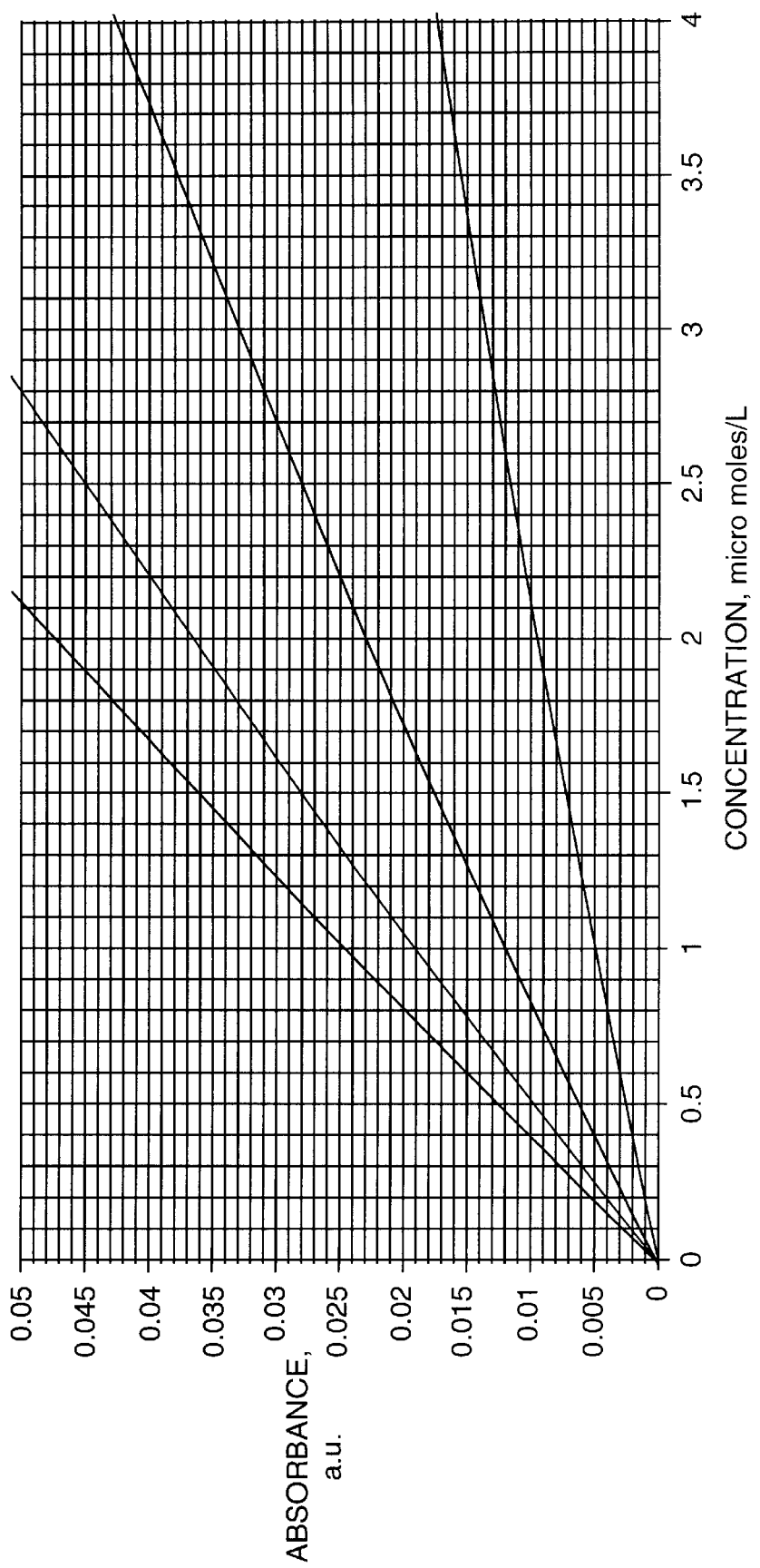

FIG. 8 shows plots of absorbance versus concentration for various levels of mobile phase absorption. For the case modeled, the long pathlength is 50 mm, the short path 0.5 mm (j=0.01) and the light is divided equally between the paths in the absence of mobile phase absorption (X=0.5). Compare these with FIG. 6 for the single path cell.

There are three regimes in the dual cell A versus c plots. At low concentration the long path dominates giving high sensitivity. The short path behaves as an extra source of stray light. At mid concentrations the long path becomes opaque at the analytical wavelength, and from there to high concentrations the light leaving the cell is dictated by absorption in the short path. At very high concentrations, stray light has the ultimate say, causing the curve to flatten out. These regions are shown in FIG. 5.

For a non-absorbing mobile phase, Equation 16 leads to:

$$A_{intercept} = \log[1/1+X], \text{ and } A_{roll-off} = \log[1/k]$$

which allows X and k to be estimated from the calibration curve. Table I is an example of the dependence of $A_{intercept}$ on mobile phase absorption. The pathlength ratio is j=0.01. $A_m$=1.0 is a high value in practice, but can be encountered, for example, with methanol of a TFA gradient at short wavelengths.

TABLE I

| $A_m$ | $A_{intercept}$ X = 0.5 k = 0 | $A_{intercept}$ X = 0.5 k = 0.001 | $A_{intercept}$ X = 0.8 k = 0 |
| --- | --- | --- | --- |
| 0.0 | 0.3010 | 0.3006 | 0.699 |
| 0.2 | 0.2132 | 0.2129 | 0.548 |
| 0.4 | 0.1467 | 0.1464 | 0.416 |
| 0.6 | 0.0985 | 0.0984 | 0.305 |
| 0.8 | 0.0650 | 0.0649 | 0.216 |
| 1.0 | 0.0423 | 0.0422 | 0.149 |

Typical amounts of stray light have a negligible effect on the extrapolation to find $A_{intercept}$.

Equation 17 shows that the high c slope is ε.j.b, the same as a single path cell with the short path. It does not change when typical levels of mobile phase absorbtion are present, because the path is so short. The initial slope is obtained from Eq. 17 with c=0. This can be written $(dA/dc)_{init}$=ε.b. (initial slope factor). Table II is an example of the effect of mobile phase absorption on the initial slope. The long pathlength b=50 mm, j=0.01 and ε.=$10^4$ cm$^{-1}$(M/L)$^{-1}$. If $A_m$=0, $(dA/dc)_{init}$=ε.b.X

TABLE II

| $A_m$ | Initial slope factor X = 0.5 k = 0 | Initial slope factor X = 0.5 k = 0.001 | Initial slope factor X = 0.8 k = 0 | High concentration slope |
| --- | --- | --- | --- | --- |
| 0 | 0.505 | 0.504 | 0.802 | 500 |
| 0.2 | 0.394 | 0.394 | 0.720 | 500 |
| 0.4 | 0.294 | 0.293 | 0.620 | 500 |
| 0.6 | 0.211 | 0.211 | 0.510 | 500 |

TABLE II-continued

| $A_m$ | Initial slope factor X = 0.5 k = 0 | Initial slope factor X = 0.5 k = 0.001 | Initial slope factor X = 0.8 k = 0 | High concentration slope |
|---|---|---|---|---|
| 0.8 | 0.148 | 0.147 | 0.398 | 500 |
| 1.0 | 0.102 | 0.102 | 0.298 | 500 |

One purpose of the dual path cell is to extend the range of analyte concentrations which can be measured accurately. FIG. 5 represents a generalized calibration curve, A versus c. The following analysis puts no limits on the shape of the curve, except that its slope must always be positive. The analysis applies to single, double or multipath cells.

The following quantities can be defined with reference to FIG. 5:

$\Delta A$: the smallest detectable change in absorbance equal to the noise on the detector output when the output is A.

$A_0$: the baseline absorbance noise—smallest detectable change in absorbance when the cell is filled with pure mobile phase, A=0.

$\Delta c$: the smallest detectable change in concentration corresponding to $\Delta A$. dA/dc: the slope of the calibration curve at concentration c.

The detector's analytical precision $\Delta c/c$ can be calculated from the slope of the calibration curve (dA/dc), and the absorbance noise $\Delta A$ at absorbance A when the analyte concentration is c. The relationship is written conveniently as:

$$\Delta c/c = (dc/dA) \cdot \Delta A/c \qquad (\text{Eq. 18})$$

Figure 7:
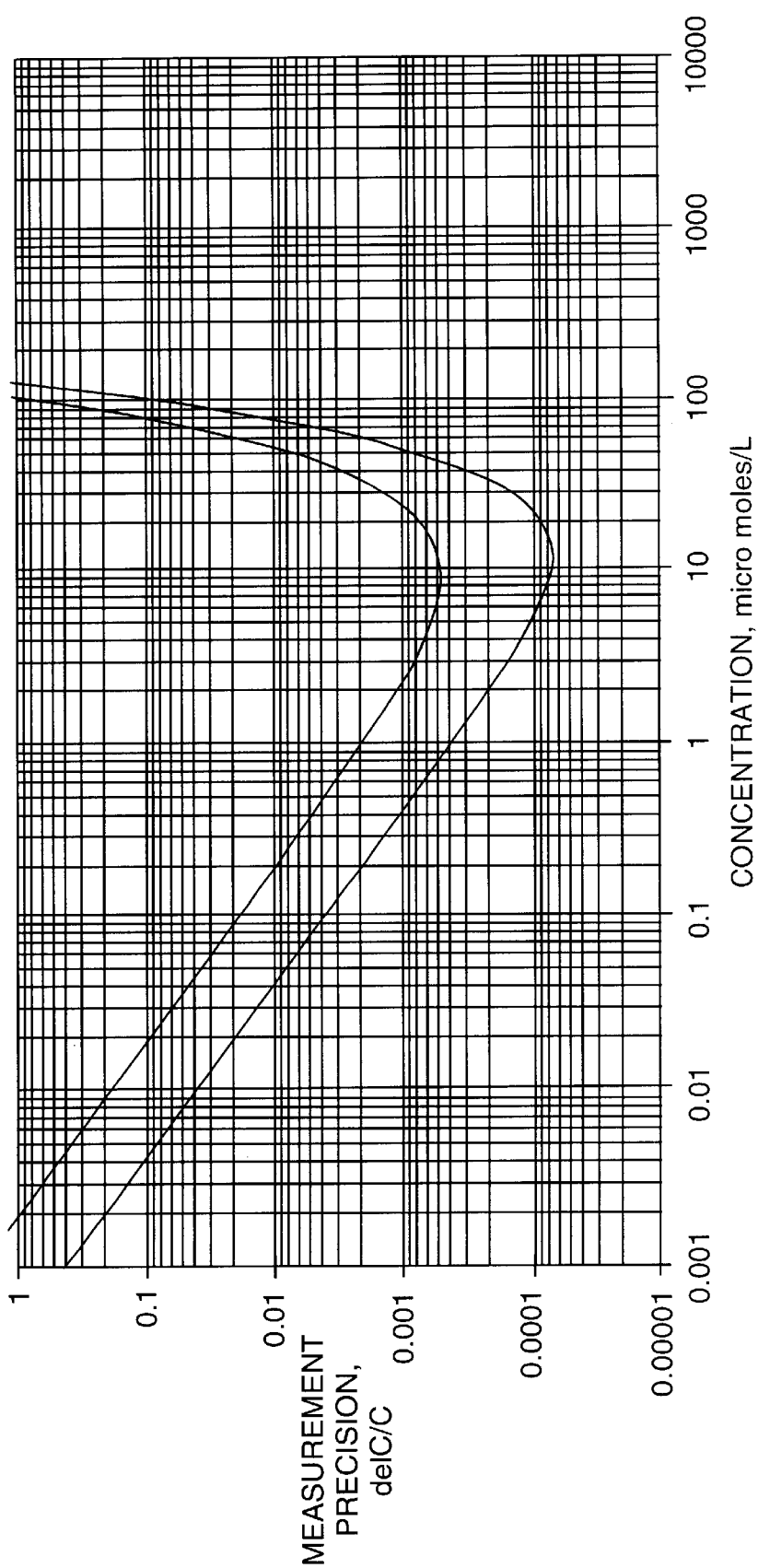
FIG. 7 is a graph illustrating Ac/c versus c for a single path flow cell with a length of 50 mm.
Figure 9:
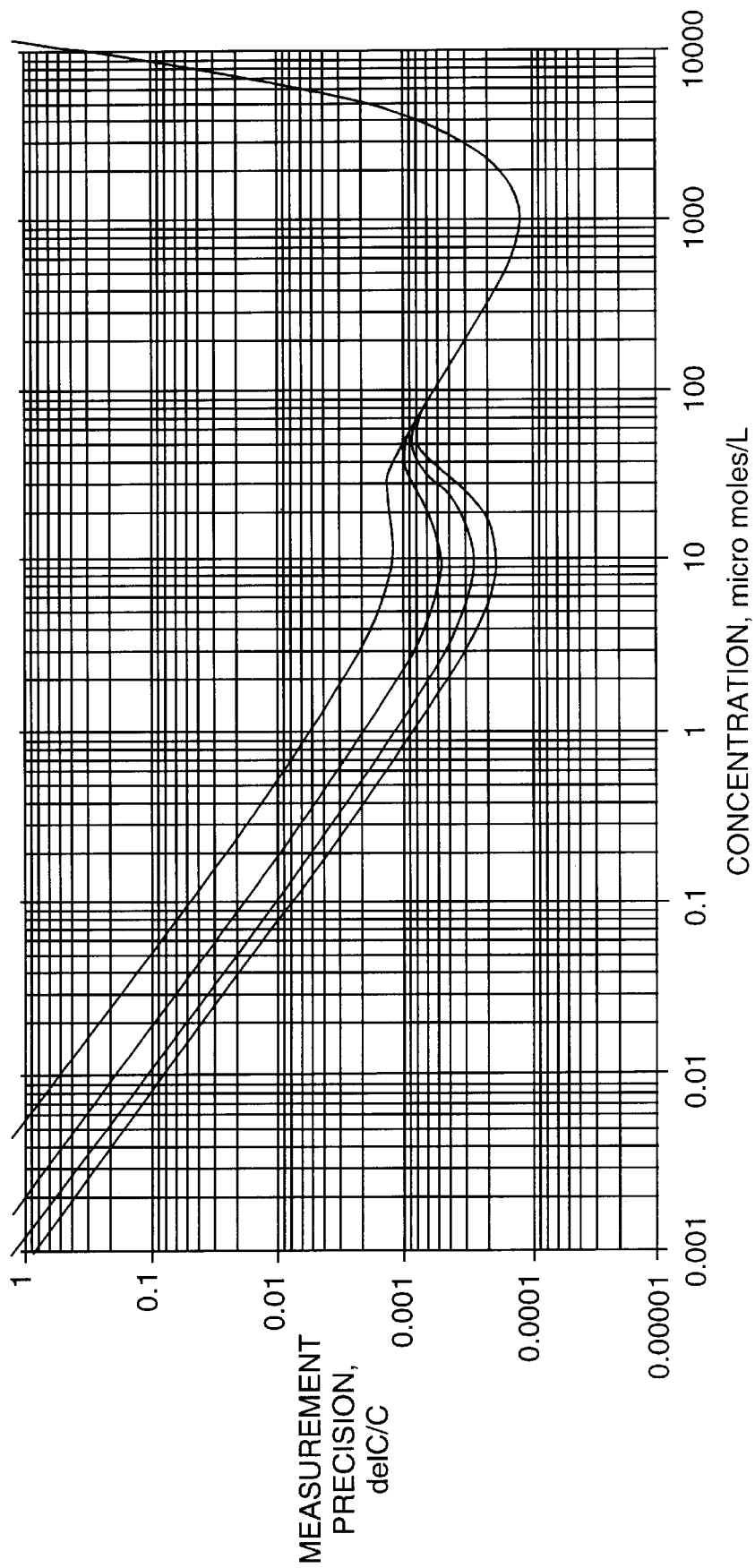
FIG. 9 is a graph illustrating Δc/c versus c for dual path flow cells with X=0.5 and k=0.1%.
Figure 10:
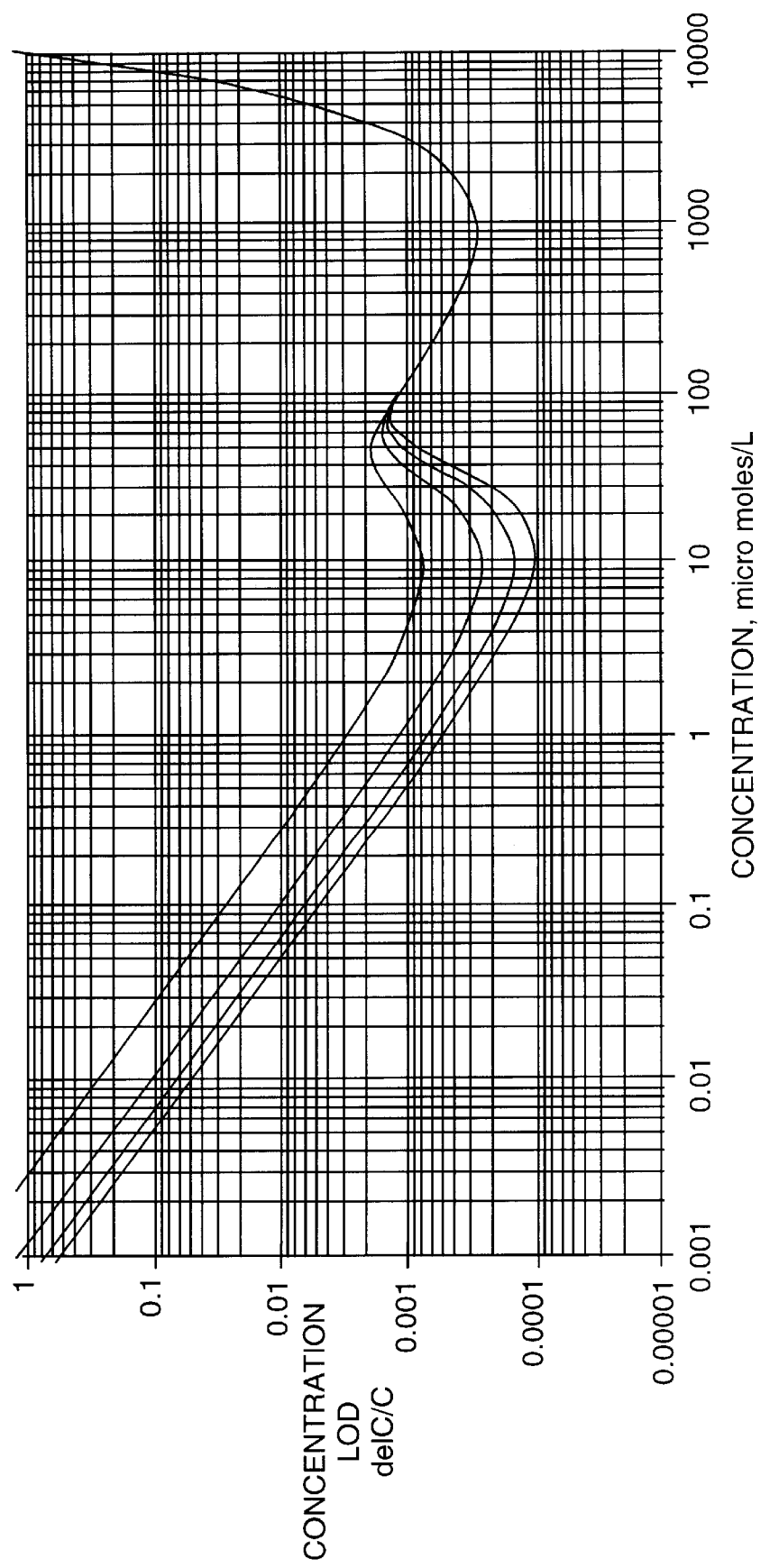
FIG. 10 is a graph illustrating Δc/c versus c for dual path flow cells with X=0.8 and k=0.1%.

The analytical precision plots, FIGS. 7, 9 and 10, show the range of concentrations which can be measured accurately. When $\Delta c/c=1$, an analyte's absorbance is equal to the baseline noise and c is the concentration limit of detection (LOD). When $\Delta c/c$ is below 0.01, its concentration can be measured to better than 1%.

Absorbance noise varies with sample absorbance, increasing as light is absorbed by the sample. It is possible to characterize the noise sources in the detector and predict $\Delta A$ at any signal level I. Alternatively, in a typical absorbance detector, the baseline signal level $I_0$ covers a wide range of values across the measured spectrum. A record of the baseline signal over a short period of time at different wavelengths provides the same $\Delta A$ versus I information. This last approach has the advantage of including system related effects such as pump and mobile phase dependent fluidic noise. It is particularly easy to obtain these data for a PDA detector, since noise can be measured simultaneously at all wavelengths.

Results, using noise data from a Waters Corporation 996 PDA detector, are shown in FIG. 7 (for a single path cell), and FIGS. 9 and 10 (for a dual path cell). The improvement in concentration range (ratio of high c to low c where c can be measured to 1% or better) using the dual path cell is apparent. The cost is loss of very high analytical precision indicated by the minimum in FIG. 7, which in fact can never be realized in a practical analytical situation. Note again that performance at high concentrations is unaffected by mobile phase absorption.

Table III shows concentration ranges of single and dual path cells. Concentration can be measured to 1% or better between the limits listed below.

TABLE III

| FIG. | long path b mm | short path b.j mm | X | $A_m$ a.u. 50 mm path | Low c -for $\Delta c/c = 0.01$ | High c | Range High c/ Low c |
|---|---|---|---|---|---|---|---|
| Single path: | | | | | | | |
| 7 | 50 | | 1 | 0 | 0.038 | 72 | 1,900 |
|   |    |   |   | 1 | 0.18 | 50 | 278 |
| 8 |    | 0.5 | 0 | 0 | 3.8 | 7,200 | 1,900 |
|   |    |   |   | 1 | 3.8 | 7,200 | 1,900 |
| Dual path: | | | | | | | |
| 11 | 50 | 0.5 | 0.5 | 0 | 0.077 | 6,700 | 87,000 |
|    |    |     |     | 0.2 | 0.109 | 6,700 | 61,500 |
|    |    |     |     | 0.5 | 0.180 | 6,700 | 37,200 |
|    |    |     |     | 1.0 | 0.505 | 6,700 | 13,300 |
| 13 | 50 | 0.5 | 0.8 | 0 | 0.048 | 5,650 | 117,700 |
|    |    |     |     | 0.2 | 0.063 | 5,650 | 90,000 |
|    |    |     |     | 0.5 | 0.100 | 5,650 | 56,500 |
|    |    |     |     | 1.0 | 0.280 | 5,650 | 20,200 |

Table III shows some interesting results. First, 0.1% stray light makes no significant difference to the above numbers. With 0.1% stray light, the single path, high concentration limit must be reduced by 30% to 40% if the requirement is to stay within the linear Beer's Law region. Finally, the dramatic effect of mobile phase absorption is actually worse for the long single cell than the dual cell. ($A_m$ is the absorbance of mobile phase in a 50 mm path).

Calibration strategies for a dual path cell according to the present invention will now be compared with those for a single path cell. A single path cell yields a calibration curve $A=\epsilon \cdot b \cdot c$ which goes through the origin and has a slope $\epsilon \cdot b$. Current calibration practice consists of the following steps, measurements being made over a spectral range (PDA) or at a selected analytical wavelength (tunable detector):

1. Scan the baseline with pure mobile phase in the cell to establish zero absorbance.
2. Measure the absorbance of a series of known concentrations of analyte in the mobile phase and plot a calibration curve. Note where the curve departs from acceptable linearity, and restrict quantitation to absorbances below this point.

Step 2 takes account of both mobile phase absorption and stray light on detector linearity.

A dual cell is characterized by two pathlengths, b and j.b, and the fraction X of light in the long path when nothing in the cell absorbs. At low concentrations, the shape of the calibration curve is affected by mobile phase absorption, a distinct difference from the single path cell. Calibration of a dual path cell characterizes the non-linearity of the calibration curve to exploit the increased concentration range. One strategy requires the following steps, but it should be appreciated that other strategies are possible:

Step 1: Determine the pathlength ratio j from the design of the cell

Step 2: Scan the baseline first with pure water in the cell ($I_0$) then with pure mobile phase ($I_m$). The ratio ($I_m/I_0$) is the transmittance of the mobile phase.

Step 3: Measure the transmittance of a range of concentrations of the analyte of interest ($I/I_m$) and fit data at each wavelength to the equation below (Eq. 19) with X as an adjustable parameter. The transmittance roll-off $I_{roll-off}/I_o$ at high c gives k.

Combine equations 13 and 15, assuming $10^{-jA_m}=1$, and that k has negligible effect on the measurement of mobile phase absorption:

$$(I_m/I_o - (1-X))e^{-\alpha bc} + (1-X)e^{-\alpha jbc} = (I/I_m)(I_m/I_o) - k \qquad (\text{Eq. 19})$$

Pure water is the most transparent of solvents in the UV. Even so, its absorbance increases rapidly below 200 nm, reaching about 0.13 au. at 190 nm for a 10 mm path. Appropriate correction should be made to the $I_O$ data at wavelengths below 200 nm.

Although the present invention has been described in terms of dual path systems, multiple paths are possible. The paths may be discrete and separated, or the light paths may merge in their passage through the cell. The common feature according to the invention is that light takes two or more paths of significantly different length through the sample before it is combined onto a single photodetector, or onto the elements of a photo detector array. It will be apparent that the distribution of light in the various paths can be chosen to optimize the properties of the cell, in particular to increase the concentration range for accurate quantitation.

While the dual path flow cell embodiment described herein includes Teflon AF coated on various surfaces to effect light guiding, it will be appreciated that other materials could be used to effect light guiding, as a function of the application, such as other amorphous fluoropolymers.

Similarly, while the Teflon AF light guiding material is described in the embodiments herein as coatings applied to at least one of the interior surface of the outer wall of the flow cell and the interior of the fused silica tube, it should be appreciated that the amorphous flouropolymer coatings could be applied to the interior and the exterior surfaces of the silica tube with similar effect, and the light guiding materials could be provided as other than coatings, such as by disposing films adjacent to the relevant surface(s).

Although the invention has been shown and described with respect to exemplary embodiments thereof, various other changes, omissions and additions in the form and detail thereof may be made therein without departing from the spirit and scope of the invention.

What is claimed is:

1. An absorbance detector apparatus, comprising:
   a flow cell having a chamber receiving a sample, said chamber being configured to provide at least a first light path through said sample and a second light path through said sample, said first light path being longer than said second light path;
   a light source directing light into said flow cell and into said at least said first light path through said sample and said second light path through said sample; and
   a single photo detector or single photodetector array receiving light exiting from said at least said first light path through said sample and said second light path through said sample;
   wherein concentration of the sample relates to the measured absorbance by the equation set forth below:

$$A=\log(I_m/I)=\log[(X.10^{-Am}+(1-X).10^{-jAm}+k)/(X.10^{-Am}.e^{-\alpha bc}+(1-X).10^{-jAm}.c^{-\alpha jbc}+k)]$$

and the letters and symbols have the following meanings:
   A represents absorbance of the analyte;
   $I_m$ represents the signal of a detector relating to the light transmitted through the mobile phase,
   I represents the signal or a detector relating to light transmitted in the presence of analyte;
   X represents the fraction of light passed by the first light path absent mobile phase and analyte absorbtion;
   (1−X) represents the fraction of light passed by the second light path absent mobile phase and analyte absorbtion;
   b represents the length of the first light path;
   jb represents the length of the second light path;
   Am represents the absorbance of the mobile phase;
   k represents a constant relating to stray light;
   α represents the absorbtion coefficient of the an analyte;
   c represents the concentration of the analyte; and,
   c represents the base of natural logarithms.

2. The absorbance detector apparatus of claim 1 wherein said flow cell comprises a light transparent material shorter than said first light path to establish said second light path, the refractive index of said transparent material being greater than the refractive index of said sample.

3. The absorbance detector apparatus of claim 2 wherein said light transparent material is a tube.

4. The absorbance detector apparatus of claim 3 wherein said tube comprises a fused silica tube.

5. The absorbance detector apparatus of claim 1 wherein said flow cell comprises:
   a light transparent tube disposed interior to said chamber; and
   at least one of a first light guiding material disposed adjacent to an interior surface of said chamber and a second light guiding material disposed adjacent to an interior surface of said light transparent tube,
   wherein said light transparent tube is dimensioned with respect to said chamber to form said at least said first light path through said sample and said second light path through said sample.

6. The absorbance detector apparatus of claim 5 wherein said first light guiding material is Teflon AF coated on said interior surface of said chamber.

7. The absorbance detector apparatus of claim 5 wherein said first-light guiding material is a Teflon AF tube disposed adjacent to said interior surface of said chamber.

8. The absorbance detector of claim 5 wherein said light transparent tube comprises a fused silica tube.

9. The absorbance detector of claim 5 wherein said second light guiding material is formed of Teflon AF.

10. The absorbance detector apparatus of claim 1 wherein said chamber is cylindrically shaped.

11. The absorbance detector apparatus of claim 1 wherein said chamber has a first end and a second end, and includes an inlet port proximate to said first end and an outlet port proximate to said second end, and wherein said flow cell further comprises light transparent end windows disposed at each of said first end and said second end.

12. The absorbance detector apparatus of claim 11 wherein said flow cell comprises a light transparent tube shorter than said first light path to establish said second light path, the refractive index of said light transparent tube being greater than the refractive index of said sample, and wherein at least one of said light transparent end windows is an entrance lens which cooperates with said light source to substantially prevent light rays in said first light path from impinging on an inner surface of said light transparent tube.

13. The absorbance detector apparatus of claim 11 wherein said flow cell comprises a light transparent tube shorter than said first light path to establish said second light path, the refractive index of said light transparent tube being greater than the refractive index of said sample, and wherein at least one of said light transparent end windows is an exit lens which is configured to substantially prevent light rays striking an inside bore of said tube from reaching said single photodetector.

14. A flow cell, comprising:
   a chamber receiving a sample;
   a light transparent tube disposed interior to said chamber; and
   at least one of a first light guiding material disposed adjacent to an interior surface of said chamber and a second light guiding material disposed adjacent to an interior surface of said light transparent tube, said light transparent tube is dimensioned with respect to said chamber to form at least a first light path through said sample and a second light path through said sample, said first light path being longer than said second light path;

wherein concentration of the sample relates to the measured absorbance by the equation set forth below:

$$A=\log(I_m/I)=\log[(X.10^{-Am}+(1-X).10^{-jAm}+k)/(X.10^{-Am}.e^{-\alpha bc}+(1-X).10^{-jAm}.e^{-\alpha jbc}+k)]$$

and the letters and symbols have the following meanings:

A represents absorbance of the analyte;
$I_m$ represents the signal of a detector relating to the light transmitted through the mobile phase;
I represents the signal of a detector relating to light transmitted in the presence of analyte;
X represents the fraction of light passed by the first light path absent mobile phase and analyte absorbtion;
(1−X) represents the fraction of light passed by the second light path absent mobile phase and analyte absorbtion;
b represents the length of the first light path;
jb represents. the length of the second light path;
Am represents the absorbance of the mobile phase;
k represents a constant relating to stray light;
α represents the absorbtion coefficient of the analyte;
c represents the concentration of the analyte; and,
e represents the base of natural logarithms.

15. The flow cell of claim 14 wherein said chamber is cylindrically shaped.

16. The flow cell of claim 14 wherein said first light guiding material is Teflon AF coated on said interior surface of said chamber.

17. The flow cell of claim 14 wherein said first light guiding material is a Teflon AF tube disposed adjacent to said interior surface of said chamber.

18. The flow cell of claim 14 wherein said chamber has a first end and a second end, and includes an inlet port proximate to said first end and an outlet port proximate to said second end, and wherein said flow cell further comprises light transparent end windows disposed at each of said first end and said second end.

19. The flow cell of claim 14 wherein said light transparent tube comprises a fused silica tube.

20. The flow cell of claim 14 wherein said second light guiding material is formed of Teflon AF.

21. A method of forming a flow cell, said method comprising the steps of:

providing a chamber configured for receiving a sample;

dimensioning a light transparent lube with Respect to said chamber to form at least a first light path through said sample and a second light path through said sample, said first light path being longer than said second light path; and disposing said light transparent tube interior to said chamber;

wherein concentration of the sample relates to the measured absorbance by the equation set forth below:

$$A=\log(I_m/I)=\log[(X.10^{-Am}+(1-X).10^{-jAm}+k)/(X.10^{-Am}.c^{-\alpha bc}+(1-X).10^{-jAm}.e^{-\alpha jbc}+k)]$$

and the letters and symbols have the following meanings:

A represents absorbance of the analyte;
$I_m$ represents the signal of a detector relating to the light transmitted through the mobile phase;
I represents the signal of a detector relating to light transmitted in the presence of analyte;
X represents the fraction of light passed by the first light path absent mobile phase and analyte absorbtion;
(1−X) represents the fraction of light passed by the second light path absent mobile phase and analyte absorbtion:
b represents the length of the first light path;
jb represents the length of the second light path;
Am represents the absorbance of the mobile phase;
k represents a constraint relating to stray light;
α represents the absorbtion coeffecient of the analyte;
c represents the concentration of the analyte; and,
e represents the base of natural logarithms.

22. The method of claim 21 further including a step of disposing at least one of a first light guiding material adjacent to an interior surface of said chamber and a second light guiding material adjacent to an interior surface of said light transparent tube.

23. The method of claim 22 wherein said step of disposing at least one of said first light guiding material and said second light guiding material involves coating Teflon AF on at least one of said interior surface of said chamber and said interior surface of said light transparent tube, respectively.

24. The method of claim 22 wherein said step of disposing at least one of said first light guiding material and said second light guiding material involves disposing a Teflon AF tube adjacent to at least one of said interior surface of said chamber and said interior surface of said light transparent tube, respectively.

25. The method of claim 22 wherein said step of disposing at least one of said first light guiding material and said second light guiding material involves disposing Teflon AF adjacent to at least one of said interior surface of said chamber and said interior surface of said light transparent tube, respectively.

26. The method of claim 21 wherein said chamber has a first end and a second end, and said method further involves the steps of providing an inlet port proximate to said first end and an outlet port proximate to said second end, and providing light transparent end windows at each of said first end and said second end.

27. An absorbance detector apparatus, comprising:

flow cell means for receiving a sample and for providing at least a first light path through said sample and a second light path through said sample, said first light path being longer than said second light path;

light source means for directing light into said at least said first light path through said sample and said second light path through said sample; and a single detection means receiving light exiting from said at least said first light path through said sample and said second light path through said sample;

wherein concentration of the sample relates to the measured absorbance by the equation set forth below:

$$A=\log(I_m/I)=\log[(X.10^{-Am}+(1-X).10^{-jAm}+k)/(X.10^{-Am}.e^{-\alpha bc}+(1-X).10^{-jAm}.e^{-\alpha jbc}+k)]$$

and the letters and symbols have the following meanings:

A represents absorbance of the analyte;

$I_m$ represents the signal of a detector relating to the light transmitted through the mobile phase;

I represents the signal of a detector relating to light transmitted in the presence of analyte;

X represents the fraction of light passed by the first light path absent mobile phase and analyte absorbtion;

(1−X) represents the fraction of light passed by the second light path absent mobile phase and analyte absorbtion;

b represents the length of the first light path;

jb represents the length of the second light path;

Am represents the absorbance of the mobile phase;

k represents a constant relating to stray light;

α represents the absorbtion coeffecient of the analyte;

c represents the concentration of the analyte; and, e represents the base of natural logarithms.

\* \* \* \* \*